(12) United States Patent  
Leighton

(10) Patent No.: US 6,383,801 B1
(45) Date of Patent: May 7, 2002

(54) DOUBLE Z-DRIVE TISSUE ARRAY INSTRUMENT

(75) Inventor: Stephen B. Leighton, Silver Spring, MD (US)

(73) Assignee: Beecher Instruments, Silver Springs, MD (US)

( * ) Notice: Subject to any disclaimer, the term of this patent is extended or adjusted under 35 U.S.C. 154(b) by 0 days.

(21) Appl. No.: 09/811,963

(22) Filed: Mar. 19, 2001

(51) Int. Cl.[7] ................................................ C12M 1/36
(52) U.S. Cl. ............................... 435/286.3; 435/284.1; 435/286.2; 435/307.1; 435/307.9; 422/63
(58) Field of Search .......................... 435/284.1, 286.2, 435/286.3, 307.1, 309.1; 422/63, 68.1

(56) References Cited

U.S. PATENT DOCUMENTS

| | | | | |
|---|---|---|---|---|
| 4,684,613 A | * | 8/1987 | Barrere et al. ............ | 435/286.3 |
| 4,979,093 A | * | 12/1990 | Laine et al. .................. | 700/61 |
| 5,355,304 A | * | 10/1994 | DeMoranville et al. ..... | 700/245 |
| 5,355,439 A | * | 10/1994 | Bernstein et al. ........... | 700/247 |
| 5,675,715 A | * | 10/1997 | Bernstein et al. ........... | 700/247 |
| 6,103,518 A | * | 8/2000 | Leighton ..................... | 422/63 |

* cited by examiner

Primary Examiner—David A. Redding
(74) Attorney, Agent, or Firm—Pendorf & Cutliff

(57) ABSTRACT

Arrays of biological tissue can be created by removing cores from regions of interest in a series of donor blocks of embedded tissues. The cores removed are placed in a regular array in a recipient block. This is typically done with two different punches, one for obtaining the cores of interest and the other for creating the receiving holes in the recipient block. The present invention comprises such a system including two separate z axes, one for each punch. Each punch has its own stylet and the axis of each punch is parallel to the axis of its drive.

14 Claims, 2 Drawing Sheets

DOUBLE Z-DRIVE TISSUE ARRAY INSTRUMENT

FIELD OF THE INVENTION

Arrays of biological tissue can be created by removing cores from regions of interest in a series of donor blocks of embedded tissues. The cores removed are placed in a regular array in a recipient block. This is typically done with two different punches, one for obtaining the cores of interest and the other for creating the receiving holes in the recipient block. The present invention comprises such a system including two separate z axes, one for each punch. Each punch has its own stylet and the axis of each punch is parallel to the axis of its drive.

BACKGROUND OF THE INVENTION

Biological tissue arrays consist of regular arrays of cores of embedded biological tissue arranged in a sectionable block typically made of the same embedding material used originally for the tissue in the cores. The new blocks may be sectioned by traditional means (microtomes etc.) to create multiple nearly identical sections each containing dozens, hundreds or even over a thousand different tissue types. These sections may be used for histochemical and other assays. Any test performed on any one of these sections is effectively performed on hundreds of samples at once. The result is a tremendous saving in effort and time and some increase in the availability and precision of control samples.

Tissue arrays have been constructed entirely manually (Battifora, H., "The Multitumor (sausage) tissue block: novel method for immunohistochemical antibody testing," Laboratory Investigation Vol. 55, pp. 244–248, 1986) and with the assistance of mechanical mechanisms (Kononen et al "Tissue microarrrays for high-throughput molecular profiling of tumor specimens", Nature Medicine Vol.4 Number 7 July 1998 pp. 844–847) for a variety of biological applications.

A manual instrument has been described in U.S. Pat. No. 6,103,518 (Leighton) entitled "Instrument for constructing tissue arrays". Semiautomatic systems have also been proposed. The manual methods have largely been superceded by those aided by instruments due to the speed, precision and increased density of the latter. In these devices, two hollow needle-like punches are used, one slightly smaller than the other to create a hole in a recipient block, typically of paraffin or other embedding medium. The larger punch is used to obtain a core sample from a donor block of embedded biological tissue of interest.

The punches are sized such that the sample obtained just fits in the hole created in the recipient block. Thus the sample is a snug fit in the recipient block and a precise array can be created.

The recipient block is held in an appropriate fixture during the entire process—although it may be removed and be alternated with one or more other recipient blocks to create more than one array from one set of donor blocks. Micrometer drives or other precision linear positioning means position the punches with respect to the recipient block or the recipient block with respect to the punches. It is clearly desirable that the donor punch reach exactly the same x,y position that the recipient punch reaches on the recipient block for a given setting of the micrometer drives. If it does not, the retrieved sample will not pass smoothly into the hole just created for it, but instead will be damaged or lost. It is further desirable that this motion be created reliably and inexpensively.

In a co-pending application in which the present inventor is a co-inventor, it is taught to use slides and drive mechanisms to first move the recipient punch into a central position and alternately, the donor punch. This mechanism is cumbersome, expensive, slow and prone to misalignment errors. The use of slides at an intermediate angle such as 45 degrees, as taught in this application is particularly problematic, as small errors in height positioning can lead to corresponding errors in lateral position and vice versa. In other prior art (Leighton), a turret or other means allows the two punches to share a single z axis slide or drive. This mechanism is appropriate for a simple, manually operated instrument, but awkward for an automated instrument in which all motions are driven by powered actuators (pneumatic, electric etc.). Special mechanisms must be machined and assembled, and standard components are not available. It must be noted in all of the prior art it was taught that the two different punches should be brought to the same position with respect to the laboratory frame of reference as well as with respect to the pallet holding the donor and recipient blocks with a dedicated mechanism and without the use of the xy drives that might be present for moving to successive locations. Apparently the primary goal of putting the donor cores in the same holes that had been created by the recipient punches blinded the prior inventors to the possibility of doing this at two different locations. It may also have been thought that the x-y drives were not accurate enough to guarantee that correct alignment could be obtained.

SUMMARY OF THE INVENTION

It is the purpose of the present invention to overcome the cumbersome quality and slow speed of the prior art and to provide a simple precise means of alternately positioning the two punches in any tissue array instrument. In addition, it is the purpose of the present invention to provide a means for constructing a robust automated instrument.

The invention comprises completely separating the two punches (donor and recipient), giving each their own stylet (unlike the above-described device) and each their own z-drive (unlike Leighton). The x and y drives that must be present to bring different areas of the donor and recipient blocks into position under the punches in any arrayer can be simply programmed with appropriate offset values to position the point of interest under either punch in turn as required.

Since this offset value is now used in the control, it may also be used for a further improvement: The positions of the tips of the two punches can be periodically measured automatically by sensors mounted on the same pallet as the donor and recipient blocks. Whenever their positions may have moved (perhaps due to encountering a more dense block or irregularity, or perhaps by being disturbed by an operator or foreign object, or simply being altered by virtue of a new punch being installed) then the new positions can be measured and automatically used to update the offset value. This novel combination of a) sensing the tip positions with a sensor mounted on the block holding pallet with b) two different z drives allows a system to be constructed with standard components and to be robust in the face of environmental challenges and mechanical drift.

Each z drive moves its respective punch in line with the axis of the punch. Firstly, each drive can move its punch completely out of the way of the recipient and donor blocks, for example when the other punch is being used or when the x and or y drives are being used to move different points on the blocks under the punches or for observation. Secondly, each drive can move its punch to just contact or nearly contact the surface of a block, for example for depositing a donor core into a recipient block. Thirdly, each drive can move its punch into the blocks, for example for obtaining and removing a blank core from a recipient block or a tissue core from a donor block.

Since each of the two drives can move its punch into and out of the way as well as to cause it to touch or penetrate the appropriate block, only two drives are required for two punches. In the co-pending application in which the present inventor is co-inventor, four drives are required, two for moving the two punches into and out of position, and two for moving the punches into and out of the blocks. In Leighton, manual operation is contemplated, but were the system to be automated, two drives would be required, but they would need to be of two different types, one for toggling the turret from one position to the other, and another for moving the turret up and down. This would result in greater costs, as two different types of drives would be required to be designed and manufactured for the two different types of motion. In the present invention, the two drives can be identical, leading to reduced costs and simplicity.

It is within the scope of this invention to use more than two punches, each with its own drive, for example to permit quick changes between different sizes of punches for different applications.

The rest of a system using this improvement may be similar to that already described in the prior art. For example, powered or manual micrometer drives or the like may be used to position the punching mechanism over the blocks or the blocks under the punching mechanism. A removable bridge may be used for supporting the donor blocks over the recipient blocks, or the donor blocks may be attached to the same pallet that holds the recipient blocks. The latter arrangement allows the same x and y drives and slides to be used for both donor and recipient blocks.

The foregoing has outlined rather broadly the more pertinent and important features of the present invention in order that the detailed description of the invention that follows may be better understood, and so that the present contribution to the art can be more fully appreciated. Additional features of the invention will be described hereinafter, which form the subject of the claims of the invention. It should be appreciated by those skilled in the art that the conception and the specific embodiments disclosed may be readily utilized as a basis for modifying or designing other tissue arrayers for carrying out the same purposes of the present invention. It should also be realized by those skilled in the art that such equivalent structures do not depart from the spirit and scope of the invention as set forth in the appended claims.

BRIEF DESCRIPTION OF THE DRAWINGS

For a fuller understanding of the nature and objects of the present invention reference should be made by the following detailed description taken in with the accompanying drawings in which.

DETAILED DESCRIPTION OF THE INVENTION

Figure 1:
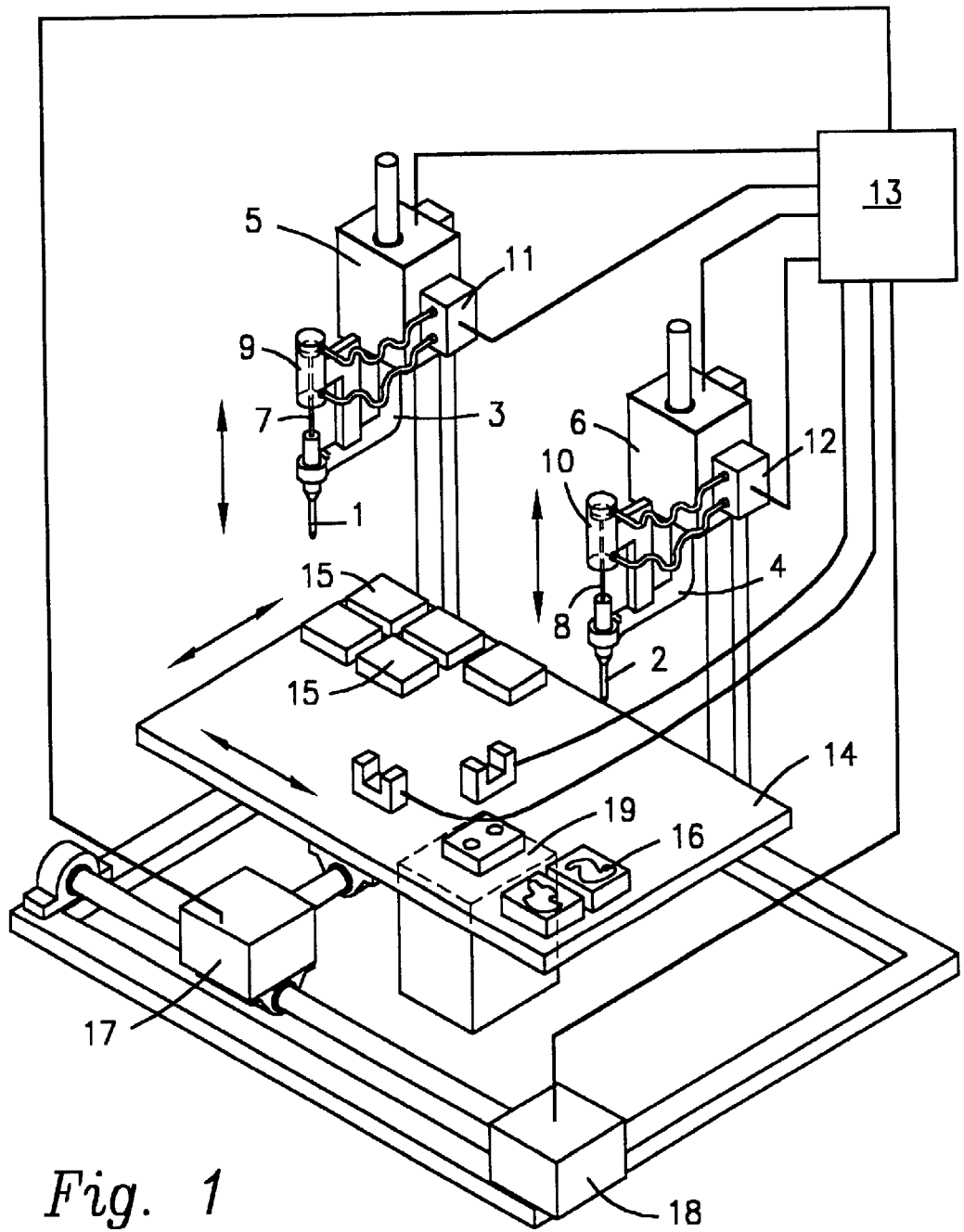
FIG. 1 is an isometric semi-schematic drawing of the invention, seen from the operator's perspective.

The present invention provides a means for constructing tissue arrays that is simple, fast and easy to automate. The improvements over the prior art are in large part attributable to using separate z axes, one for each punch.

Additional novel features are discussed below.

Wadding or Packing at the End of the Stylets

Wadding or packing may be provided at the end of the stylets to seal the gap between the stylet and the punch to keep the core from being extruded along the stylet and damaged and/or lost.

In the prior art, the stylets are metal wires sliding in the metal punch tubes. This rather crude arrangement is functional but, depending on the tissue type, temperature and closeness of fit of the wire and the tube, some of the tissue can extrude between the wire and the tube, leading to unpredictable losses of tissue. In addition to the simple loss of the tissue, this causes the additional problem of a different volume of tissue beneath the stylet and arrays being constructed with non-uniform depths. This non-uniformity leads to a much reduced yield of useful sections that can be cut from the array block.

The present invention comprises the use of small pieces of wadding or packing at the tips of the stylets to prevent this extraneous extrusion. These pieces can preferably be elastomeric material such as polyurethane, natural rubber or polyvinyl chloride or the like. They can be made to fit the punches exactly by using the punch as a tool to punch exactly the correct size disc from a sheet of the chosen material.

Force Control of the Stylet

A drive for one or both stylets can be designed to exert prescribed forces as well as moving to precise positions, to allow tamping of the cores for better grip by the punches and easier removal of the cores from the blocks.

The closest system of which the inventor is aware for automated tissue arrayers uses only positional control of the stylet. This has the disadvantage that the stylet can only be withdrawn entirely out of the way of the tissue or wax cores while they are being acquired or pushed down flush to the end of the punch to insert the tissue core in a recipient block. Although intermediate positions are possible in theory, they are not useful as the automated machine has no information on the exact length of the wax plug with which to calculate an appropriate intermediate position for the stylet. There are combinations of tissue type, wax type, temperature and punch geometry for which it has been a problem to reliably extract the core from the block. Although the punch may have cut out a core, it is not removed because it is still held at the bottom by the block and there is not enough friction along the sides of the punch to grip the core and break the connection to the block at the bottom.

The present invention includes controlling the force applied to the stylet such as by means of a pneumatic or hydraulic cylinder. This controlled force can be set high enough to push the core completely out of a punch into a tissue block or at an intermediate value for tamping the core just before it is withdrawn. The tamping compresses the core axially and thus expands it radially against the cylindrical walls of the punch. This increased radial force creates a stronger grip of the punch on the core and enables the punch to extract the core. This phenomenon is somewhat counter-intutitive as some users of earlier automated machines thought that the axial force would push the core completely out of the punch. Indeed it would push it out if large forces were used to force the stylet all the way to the end of the punch tube. Earlier descriptions of automated machines teach simple cycles involving the stylet either being at one end of its full stroke or the other.

The controlled force may be exerted by any number of ways well known in the art, such as pneumatics, hydraulics, controlled current motors, feedback systems involving force sensors on any sort of actuator or combinations of springs and various mechanisms.

The invention will now be described in greater detail by reference to the embodiment illustrated in the figures.

In FIG. 1 punches 1 and 2 are held by arms 3 and 4 and are moved vertically by drives 5 and 6. Stylets 7 and 8 are provided, respectively, for each of the two punches. They are moved vertically with respect to the punches by actuators 9 and 10. Drives 11 and 12 are provided for the stylet actuators. A computer 13 controls all of the drives or actuators. A pallet 14 is moved in the x and y directions by actuators 17 and 18. The pallet holds recipient blocks 15, donor blocks 16, a waste receptacle 19 and sensors 20. The sensors 20 detect the stylets allow the computer to find the position of the punches with respect to the pallet. Other sensors, limit switches, encoders and feedback elements may be necessary but are not shown for clarity since their use is well know in the art. For this purpose, U.S. Pat. No. 6,103,518 and 6,136,592 are incorporated herein by reference.

Figure 2:
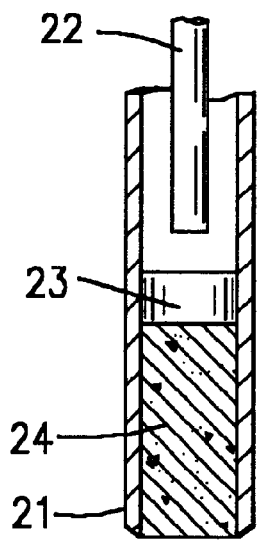
FIG. 2 is a longitudinal cross-section of one of the punch/stylet assemblies.

Turning now to FIG. 2, there is shown punch 21, a stylet 22 within the punch, a piece of wadding or packing 23 and a tissue or wax core 24.

Figure 3:
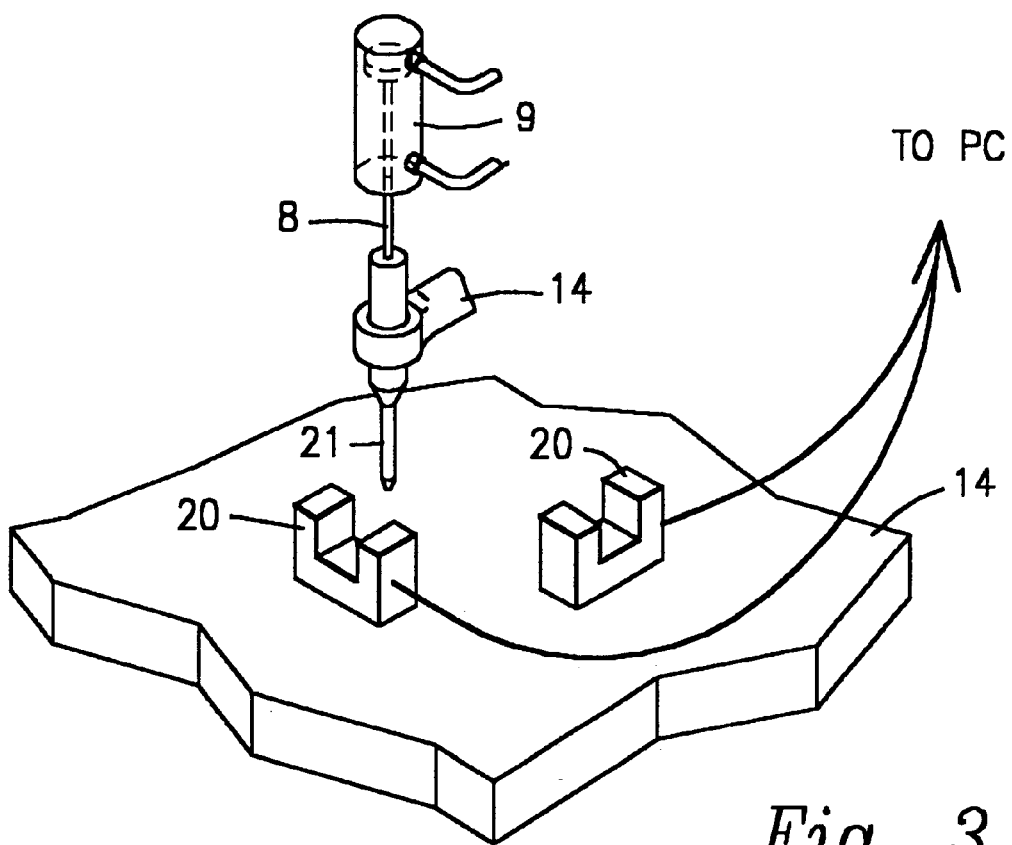
FIG. 3 is an enlarged view of one of the punches and its relationship to the sensors as shown in FIG. 1.

FIG. 3 is an enlarged view of one of the punches of FIG. 1, and better shows the 2-way hydraulic or pneumatic actuator 9 in relation to the sensors 20.

Although there are many ways to construct a device within the contemplation of the inventor, one preferred embodiment is described here. Two punches, a recipient punch 1 and donor punch 2, are positioned, each on a separate electromechanically actuated slide 5,6. The respective stylets 7,8 are independently driven by simple pneumatic cylinders 9,10. The pneumatic cylinders allow precise positioning of the stylets in either the fully up or fully down position, and also allow controlled forces at intermediate positions for tamping the cores, merely by adjusting the air pressure.

It would also be within the scope of the invention to use electromechanical actuators—with force sensors if necessary instead of the pneumatic cylinders. Similarly, pneumatic or hydraulic cylinders could conceivably be used for positioning the punches.

Preferably, electromechanically driven slides position a pallet 14 in the x and y axes to allow precise positioning of a set of one or more recipient 15 and donor blocks 16 under the punches. Alternatively, the pallet may be circular and may be driven in a circular motion. All that is necessary is that precise, predictable repositioning of the donor and recipient blocks relative to the punches can be effectuated. All of the motions may be under electronic and computer control by any of many well know means—limit switches, sensors, position feedback, stepper and/or servo motors and the like.

A typical cycle consists of the desired recipient position being brought under the recipient punch by the x-y drives; the recipient punch being moved by its z drive to penetrate and remove a blank core, creating a pocket for later use; the recipient punch being brought (by the x-y drives) near a waste receptacle (which may be mounted on the same x-y pallet as the blocks) and the recipient stylet being moved to discharge the blank core into the waste receptacle; the desired position of a donor block being brought by the x-y drives under the donor punch; the donor punch being moved by its z drive to penetrate and remove a desired core of tissue; the previously created pocket in one of the recipient blocks being brought by the x-y drives under the donor punch; and finally the donor punch being brought in contact or nearly in contact with the recipient block by its z drive and then its stylet being moved to implant the tissue core in the pocket created in the recipient block. Next, the lateral position is incremented with drives X and or Y to the next position and the cycle is repeated.

It is within the scope of the invention that either the blocks or the punches can be moved in x, y and z directions relative to the laboratory frame of reference—only relative motion matters in this invention.

For example, instead of being rigidly attached to a fixed base or frame, either or both z-axis drives may be mounted on horizontal positioning drives to move them with respect to the fixed base and hence with respect to the pallet instead of moving the pallet with respect to the fixed base. Alternatively, the pallet could be moved in the x direction, for example and one or both drives in the y direction. Alternatively, a positioning system based on polar coordinates could be used, with one or the motions being rotational and the other a radial motion. In fact, for example the donor blocks could be mounted on a computer driven turntable and the recipient blocks on a different turntable, with the z drives moved linearly horizontally from one turntable to the other. This linear motion would also serve to select radial positions of interest on either turntable. Alternatively, one set of block could be on an x-y table and the other on a rotary table, or each on their own x-y table.

It can be seen that there are many combinations and permutations possible with advantages for different applications. The key element that all have in common is the use of at least two separate z drives.

Further, in order to increase the range or capacity of the unattended instrument, it is possible to further provide a magazine containing donor and/or recipient blocks, either fresh or punched, wherein the magazine is operatively associated with said instrument for providing blocks to said instrument and/or receiving blocks from said instrument.

Although this invention has been described in its preferred form with a certain degree of particularity with respect to an instrument for creating micro-arrays with punches moveable on z axis, it is understood that the present disclosure of the preferred form has been made only by way of example and that numerous changes in the details of structures and the composition of the combination may be resorted (e.g., donor and recipient block holding pallet moving in z direction) to without departing from the spirit and scope of the invention.

Now that the invention has been described,

I claim:

1. An instrument for constructing arrays of tissue in a recipient block, the instrument comprising:

a platform for holding at least one donor block;

a platform for holding said recipient block;

a first punch unit mounted on a punch arm, said first punch unit comprising a recipient punch and associated stylet;

a second punch unit mounted on a punch arm, said second punch unit comprising a donor punch and associated stylet, said donor punch having an internal diameter greater than said recipient punch; and means for selectively repositioning said recipient block platform and said donor block platform relative to said first and second punches;

wherein each of said first and second punch units has its own independently operable punch drive, and wherein said first and second punch units are independently moveable along respective first and second punch axis, said punch axis being parallel and spaced apart.

2. The instrument of claim 1, wherein one or more of the platform moving means and the punch moving means are under computer control.

3. The instrument as in claim 1, wherein the donor block holding platform and the recipient block holding platform are different platforms.

4. The instrument as in claim 3, wherein one of said the donor block holding platform and recipient block holding platform is moveable in at least one of an x and y axis, and wherein the other of said platforms is formed by a turntable rotatable about the z axis.

5. The instrument as in claim 1, wherein the donor block holding platform and the recipient block holding platform are the same platform.

6. An instrument as in claim 5, wherein said donor block holding platform and said recipient block holding platform are driven along x and y axis, and wherein said punches are driven along z axis.

7. An instrument as in claim 5, wherein said donor block holding platform and said recipient block holding platform form a turntable rotatable about the z axis, and wherein either said punches or said platforms are provided with means for movement in least one of the x or y axis.

8. The instrument as in claim 1, wherein the donor punch and recipient punch are independently and simultaneously capable of movement in the z axis.

9. An instrument as in claim 1, further comprising an amount of compliant wadding material provided inside the punch at the tip of one or more of the stylets.

10. An instrument as in claim 1, wherein said compliant wadding material is an elastomer.

11. An instrument as in claim 1, wherein one or more of said stylets is driven by an actuator which can exert controlled forces.

12. An instrument as in claim 1, wherein the stroke length of one or more of said stylets can be controlled via said stylet actuators.

13. An instrument as in claim 12, wherein the stylet actuators are controlled for stroke length via a computer.

14. An instrument as in claim 1, further comprising a magazine containing blocks, and operatively associated with said instrument for providing blocks to said instrument and/or receiving blocks from said instrument.

* * * * *